United States Patent
Branson et al.

(10) Patent No.: US 7,176,024 B2
(45) Date of Patent: Feb. 13, 2007

(54) BIOREACTOR FOR GROWING BIOLOGICAL MATERIALS SUPPORTED ON A LIQUID SURFACE

(75) Inventors: R. Edward Branson, Chapel Hill, NC (US); Keith Everett, Pittsboro, NC (US); Bob Hester, Morrisville, NC (US); Timothy B. Vickers, Chapel Hill, NC (US)

(73) Assignee: Biolex, Inc., Pittsboro, NC (US)

( * ) Notice: Subject to any disclaimer, the term of this patent is extended or adjusted under 35 U.S.C. 154(b) by 153 days.

(21) Appl. No.: 10/845,914

(22) Filed: May 14, 2004

(65) Prior Publication Data

US 2004/0259239 A1  Dec. 23, 2004

Related U.S. Application Data

(60) Provisional application No. 60/474,479, filed on May 30, 2003.

(51) Int. Cl.
*C12N 5/00* (2006.01)

(52) U.S. Cl. .................. 435/420; 435/292.1; 47/1.4; 47/39; 47/DIG. 6

(58) Field of Classification Search .............. None
See application file for complete search history.

(56) References Cited

U.S. PATENT DOCUMENTS

| | | |
|---|---|---|
| 3,218,758 A | 11/1965 | Konikoff |
| 3,224,143 A | 12/1965 | Tew et al. |
| 3,814,680 A | 6/1974 | Wood |
| 3,928,142 A | 12/1975 | Smith |
| 3,959,923 A | 6/1976 | Selke |
| 4,676,956 A | 6/1987 | Mori |
| 4,724,214 A | 2/1988 | Mori |
| 4,874,225 A | 10/1989 | Pruszenski, Jr. |
| 5,137,828 A | 8/1992 | Robinson et al. |
| 5,447,629 A | 9/1995 | Chaumont et al. |
| 5,614,378 A | 3/1997 | Yang et al. |
| 5,846,816 A | 12/1998 | Forth |
| 6,174,720 B1 | 1/2001 | Oxley et al. |
| 6,348,347 B1 | 2/2002 | Hirabayashi et al. |
| 6,391,638 B1 | 5/2002 | Shaaltiel |

(Continued)

FOREIGN PATENT DOCUMENTS

EP  0 239 272  9/1987

(Continued)

*Primary Examiner*—David Redding
(74) *Attorney, Agent, or Firm*—Alston & Bird LLP

(57) ABSTRACT

A bioreactor assembly of the present invention for holding a media and supporting growth of a plurality of plants. The assembly includes a light source and a container having a light transmissive wall structure and defining a reservoir. A major axis of the reservoir is substantially horizontal allowing the reservoir to be filled with media to a partial level and to define a relatively large surface area for support of the plants. The assembly may also include clamps to secure and seal separate wall structure portions of the container together, and end caps to the wall portions, to define an aseptic environment. As another option, the clamps may define openings therethrough that allow passage of various devices for measuring and controlling bioreactor function such as a gas supply nozzle, a gas exit nozzle, an air temperature probe, a pH probe, a sampling drain, a gas composition probe and a media temperature probe.

34 Claims, 12 Drawing Sheets

U.S. PATENT DOCUMENTS 6,492,149 B1   12/2002   Muller-Feuga

FOREIGN PATENT DOCUMENTS

| FR | 2564854 | * | 3/1984 |
| GB | 2 118 572 | | 11/1983 |
| JP | 04190782 A | * | 7/1992 |
| WO | WO94/09113 | * | 4/1994 |
| WO | WO-00/12673 | | 3/2000 |

* cited by examiner

BIOREACTOR FOR GROWING BIOLOGICAL MATERIALS SUPPORTED ON A LIQUID SURFACE

BACKGROUND OF THE INVENTION

1. Field of the Invention

The present invention is related to the use of bioreactors for holding media and promoting the growth of biological materials, and in particular transparent bioreactors for growing biological materials requiring a light source, such as aquatic plants.

2. Description of Related Art

Photo-bioreactors are devices that allow photosynthetic microorganisms to grow in a controlled manner. U.S. Pat. No. 5,846,816 to Forth ("Forth") discloses a biomass production apparatus including a transparent chamber 10 which has an inverted, triangular cross-section, as is shown in FIG. 1 of Forth. Extending through the chamber is a first conduit 22 which has a plurality of perforations along its length to allow the introduction of gasses into the chamber. Also extending through the chamber are a pair of heat exchange conduits 26 connected to a supply of heat exchange medium.

The passage of air entering through the conduit establishes a distinctive flow pattern that causes the liquid in the chamber to circulate up through a central region of the chamber, across the upper portion of the chamber below a cover 16, and down along the chamber sidewalls 20 back to the conduit, as is shown in FIG. 3 of Forth. The cover includes two vents 28 through which the circulating gases exit the chamber. Ostensibly the passage of air and circulation of the liquid ensures that the biological matter suspended therein is exposed to light and also prevents the biological matter, such as algae, from adhering to the walls of the chamber.

Although the bioreactor disclosed by Forth promotes the growth of biological matter, it is generally not useful for applications requiring a sterile growth environment. The vents are open to external air which may include airborne contaminants. Such contaminants are especially troublesome for pharmacological applications wherein strict Food and Drug Administration guidelines for avoiding contamination must be met.

In addition, the constant circulation of the liquid required by Forth interferes with the growth of some types of biological matter. For instance, fully differentiated aquatic plants from the lemnaceae or "duckweed" family are freshwater plants that grow best on the surface of the water. Such surface growing plants typically prefer relatively still water to support and promote optimal growth.

Therefore, it would be advantageous to have a photo-bioreactor system for promoting the growth of plant biological materials in a relatively sterile environment isolated from contaminants. It would be further advantageous if the system were capable of promoting growth of surface growing aquatic plants, such as the duckweed family of plants.

BRIEF SUMMARY OF THE INVENTION

The above advantages are achieved and other needs addressed by a bioreactor assembly of the present invention for holding a media and supporting growth of a plurality of plants. The assembly includes a light source and a container having a light transmissive wall structure allowing light to pass therethrough and defining a reservoir filled with media and biological material. A major axis of the reservoir is substantially horizontal allowing the reservoir to be filled with media to a partial level and to define a relatively large surface area for support of plants and other biological materials that prefer such support. The assembly may also include clamps to secure and seal separate wall structure portions of the container together and end caps secured to the wall portions to maintain an aseptic environment. As another option, the clamps may define openings therethrough that allow passage of various devices for measuring and controlling bioreactor function such as a gas supply nozzle, a gas exit nozzle, an air temperature probe, a pH probe, a sampling drain, a gas composition probe and a media temperature probe.

In one embodiment, the present invention includes an assembly for holding a media and supporting growth of a plurality of plants. The assembly includes at least one light source and at least one container positioned adjacent the light source. A wall structure of the container has light transmissive properties to allow passage of light from the light source and in combination with other components defines a reservoir closed to the ambient environment. The reservoir has an elongate shape that defines a major axis generally extending in the direction of its longest dimension. In the assembly, the container is oriented so that the major axis of the reservoir is in a substantially horizontal plane with respect to gravity. In this manner, the reservoir, when partially filled with the media, creates a relatively large media surface on which the plants are supported.

In one aspect, the wall structure has an extruded shape with a constant cross-section. For instance, the wall structure may have a cylindrical, oval or rectangular cross-section. Preferred dimensions for the pipe wall structure range between 10 and 50 feet in length and between 2 and 12 inches in diameter. In cross-sections with a major axis, the major axis is preferably aligned with the substantially horizontal plane to further maximize the media surface area. For instance, two opposite corners of the rectangular cross-section could be positioned closer to the substantially horizontal plane than the remaining two corners.

In another aspect, a plurality of the containers may be used wherein the containers are arranged in a vertical stack with spacing between each of the containers. The vertical stack may be combined with electrically powered lights, such as light-emitting diodes or fluorescent lights as the light source. Light is supplied to the vertical stack by positioning the lights on both sides of the stack and potentially in the space between the containers.

Also included in the container may be one or more clamps for holding multiple portions of the wall structure together. The clamp may include one or more openings for the insertion of various sampling and control devices, such as a gas supply nozzle, a gas exit nozzle, an air temperature probe, a pH probe, a sampling drain, a gas composition probe and a media temperature probe extending into the reservoir through an opening defined in the clamp.

In another aspect, the clamp defines an opening that is sized and shaped to receive adjacent ends of the wall structure portions. For instance, the clamp may include a central band sized to extend around the clamp ends. Optionally, the clamp may have a pair of inwardly directed flanges spaced apart on opposite ends of the clamp wherein the flanges are configured to grip the ends of the wall structure portions. To facilitate gripping, the ends of the wall structure portions may flare outwardly to engage the inwardly directed flanges. Preferably, each of the clamps is constructed of an FDA approved composite material and includes a silicone seal to block contaminates from entering the container.

In an alternative embodiment, the container wall structure may define a closed reservoir having at least two spaced-apart portions each having a major axes. The major axes of the spaced apart portions lie in a common, substantially horizontal plane. In this manner, partially filling with media at one of the portions also partially fills the remaining portions and creates a media surface on which the plants are supported.

The present invention has many advantages. Overall, the bioreactor assembly allows the production of clinical and commercial scale quantities of biopharmaceuticals from genetically modified plants in a controlled, sterile and clean environment. For example, the use of containers defining reservoirs for partial filling with media provides a relatively large surface for the large-scale production of surface-borne biological materials, such as duckweed plants. In addition, use of the clamps having seals to interconnect the various portions of the container wall structure and sealed openings for insertion of various measurement and supply devices ensures a clean and aseptic environment to promote the growth of the biological materials for medical uses. The clamping system also allows for easy assembly and disassembly of the containers for maintenance and modification. The measurement and supply devices ensure that the environment within the reservoir is tightly controlled to maximize growth and expression of the biological materials therein.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Figure 1:
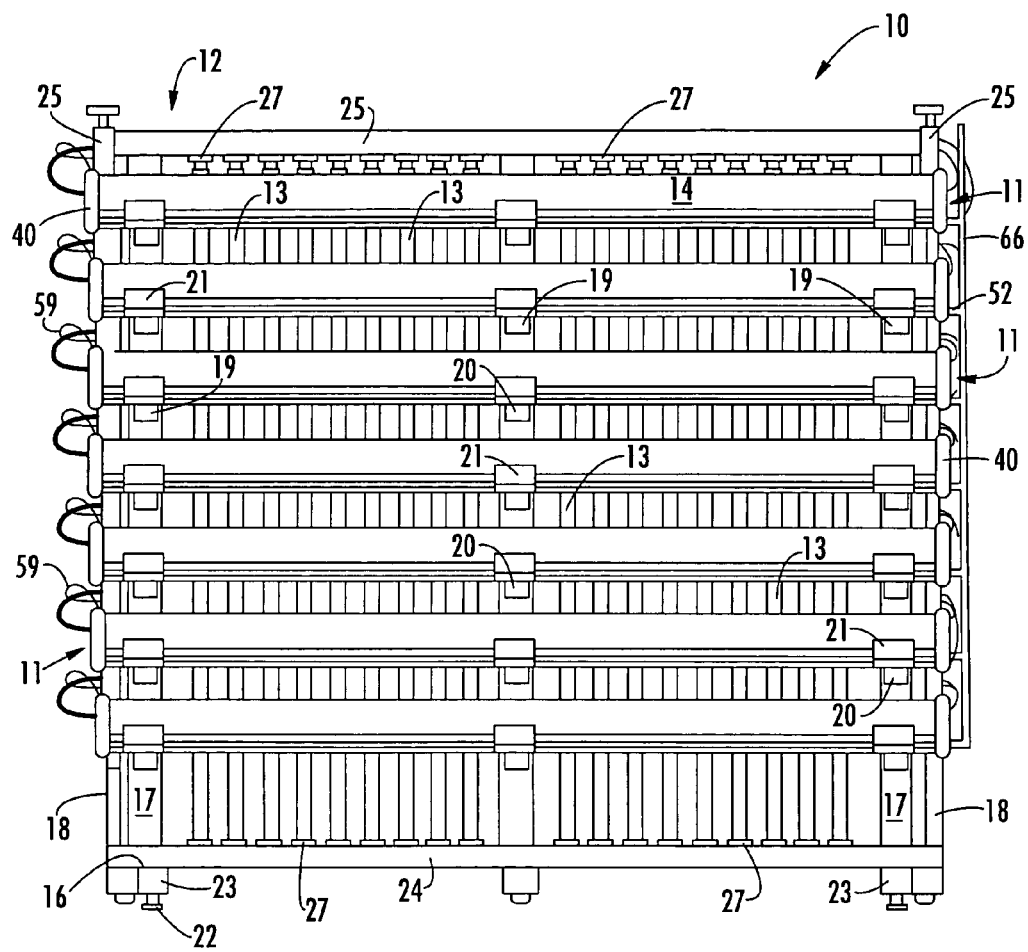
FIG. 1 is a side elevation view of a bioreactor assembly of one embodiment of the present invention.

A bioreactor assembly 10 of one embodiment of the present invention is shown in FIG. 1. Included in the bioreactor system are a plurality of substantially horizontally extending containers 11 supported by a rack 12 in a vertical stack adjacent a plurality of vertically extending lights 13. Each of the containers 11 includes a light transmissive cylindrical wall structure 14 that defines a reservoir 15 for holding media at a partially full level so as to provide a surface for supporting duckweed, or other biological material, that requires light for growth.

The term "media" as used herein refers to any liquid, gel, partially liquid-partially solid, or otherwise flowable supply of compounds, chemicals or nutrients that are used to promote the growth, testing, modification or manipulation of the biological matter housed within the reservoir 15. Media therefore, can be water alone, a combination of water with fertilizer, soil, an agar gel, mud or other combination of components, with or without water, as long as some type of flow and manipulation of the components can be induced using the devices described herein.

The term "biological materials" or "biological matter" as used herein describe any material that requires light and a supply of media in order to support proliferation or expression. Preferably, the biological materials are plants that require or thrive on liquid surfaces, such as plants within the duckweed family. Other preferred aquatic plants include Giant Salvinia, Kariba weed, Aquarium watermoss, Water Fern, Carolina mosquito fern, water hyacinth, jacinthe d'eau, Variable-leaf Pondweed, Waterthread Pondweed, Hydrilla, American Water-Plantain, Marsh Pennywort, and Creeping Rush. These plants and other biological material may be either wild plants, or transgenic plants for the production of vaccines, therapeutic proteins and peptides for human or animal use, neutraceuticals, small molecule pharmaceuticals, research and production reagents (growth factors and media additives for cell culture) or excipients for pharmaceuticals.

Figure 2:
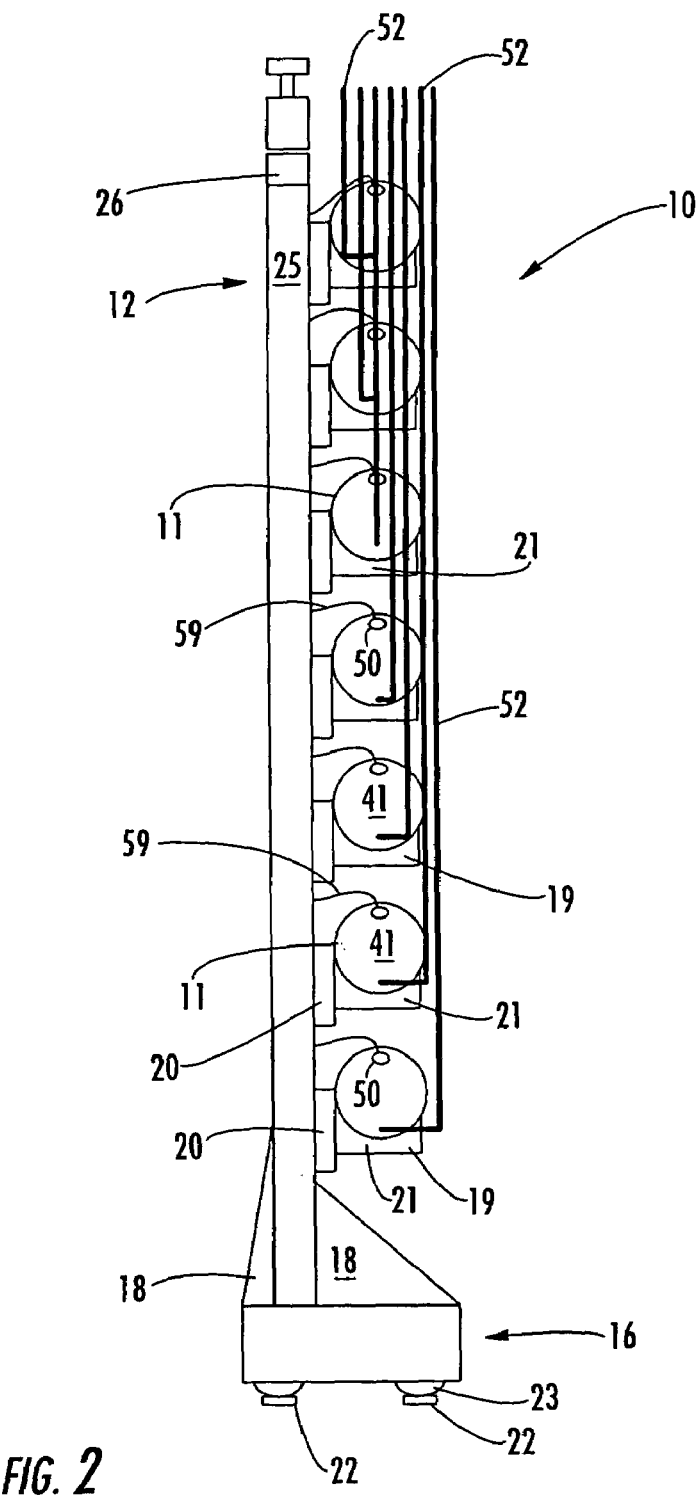
FIG. 2 is a front elevation view of the bioreactor assembly of FIG. 1.

The rack 12 of the bioreactor assembly 10 includes a base 16 for supporting the remaining portions of the rack, as is shown in FIGS. 1 and 2. In particular, the base 16 includes multiple feet 22 resting on a floor or other supporting surface at the bottom of three leg members 23 positioned at the lateral ends and center of the rack. Resting on the leg members is a support rail 24 that extends horizontally and is substantially the length of the containers 11.

Three vertical support members 17 are connected to and extend upwards from each lateral side and the center of the horizontal support rail 24. Preferably, the vertical support members 17 are supported nearer a rear edge of the base 16 so as to provide additional stability for the containers 11 which are supported on cantilevered support members 19 that extend towards a front edge of the base.

Each of the cantilevered support members 19 is mounted to a front edge of the vertical support member at regularly spaced intervals. In addition, each of the cantilevered support members includes a mounting plate 20 attached to the vertical support member 17 on its rear surface and a retaining member 21 on its front surface. As is shown in FIG. 2, the retaining member may define an arcuate upper surface congruently shaped and sized to match the outer surface of the container wall structure 14 so as to provide relatively snug support for the container.

In the embodiment illustrated in FIGS. 1 and 2, an additional pair of vertical support members 25 extend upwards from the horizontal support rail 24 of the base at the outermost ends of the horizontal support rail. A pair of gussets 18 reinforce the connection of the outermost ones of the vertical support members 25 to the horizontal support rail 24. Each of the gussets has a triangular shape with one leg attached to the horizontal support rail 24 and the other leg attached to the vertical support members 25. Because of the rearward positioning of the vertical support members, the base leg of the front one of the gussets 18 is longer than the base leg of the rear one of the gussets.

Supported at the top ends of each of the vertical support members 17, 25 is another horizontal support rail 26 that is equal in length and extends parallel to the bottom support rail 24. Both the top and bottom horizontal support rails support a plurality of light mounts 27. The light mounts are positioned in corresponding pairs extending along the rails 24, 26 at regular, spaced intervals. In this manner, each pair of light mounts can support a vertically extending one of the lights 13.

The lights 13 are preferably artificial lights that are electrically powered. For instance, lighting can be supplied by light-emitting diodes, fluorescent lights, incandescent lights, sodium vapor lights, metal halide lights or various combinations of these, and other, types of lights. Alternatively, the artificial lights may also be aided by, or replaced with, direct and indirect sunlight. However, artificial lights are preferred due to their ease of control and positioning so that all of the duckweed, or other biological material, contained in the reservoir 15 is supplied a sufficient amount of light to promote growth. Supplying power to the various types of lights can be done via wiring, or other manner that is conventional in the art and therefore not described herein in additional detail.

As noted above, the lights 13 of the embodiment illustrated in FIG. 1 have a vertical orientation (i.e., in the direction of gravity) which is perpendicular to the substantially horizontal orientation of the containers 11 held in the rack 12. The vertically-oriented lights 13 are positioned on one side of the stack of containers 11 and are spaced in parallel at regular intervals along the wall structure 14 of the containers. In this manner each light provides illumination for an adjacent section of every one of the containers 11 from one end of each of the containers to the opposite end of the container.

Figure 3:
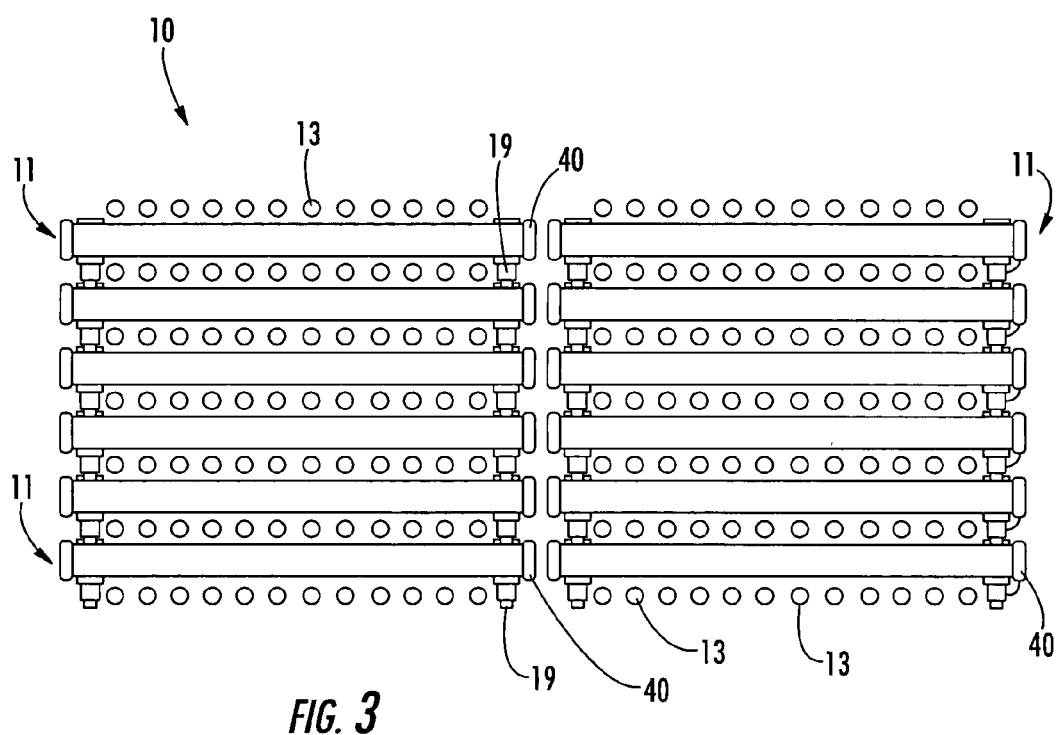
FIG. 3 is an elevation view of a bioreactor assembly of another embodiment of the present invention.

Various different configurations of the lights 13 are possible depending upon different factors such as the intensity of the lighting need to support growth, the positions of the containers 11, or the desired temperature of the media in the reservoir 15. For instance, an alternative configuration for the lights 13 is shown in FIG. 3. In this embodiment, the lights extend between the containers in a spaced, parallel arrangement. Notably, the lights in this arrangement may extend between the containers of several back-to-back vertical container stacks similar to the vertical stack shown in FIGS. 1 and 2.

Figure 4:
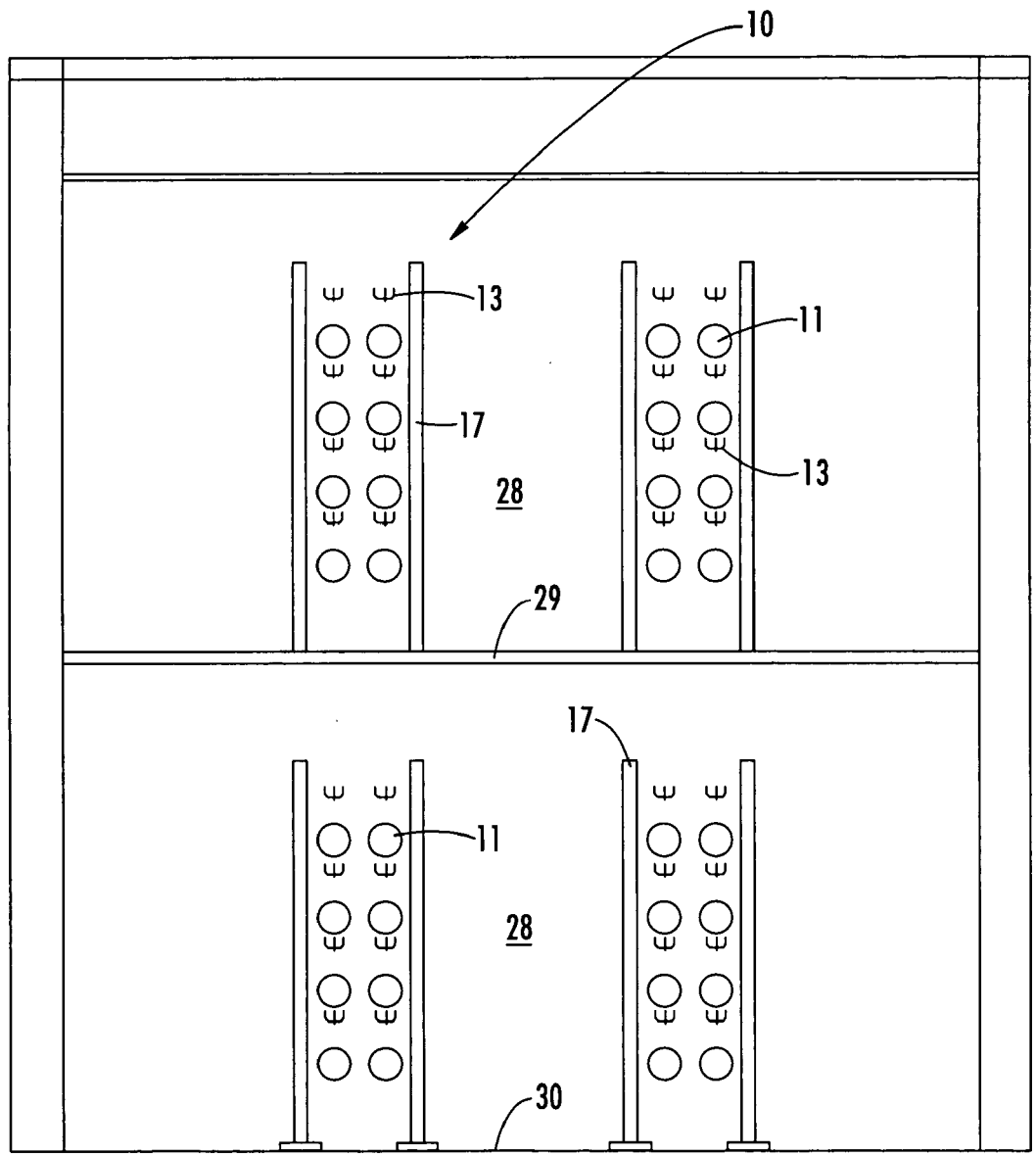
FIG. 4 is an elevation view of a bioreactor assembly of yet another embodiment of the present invention.

Another alternative configuration for the lights 13 is shown schematically in FIG. 4, wherein the lights extend horizontally in pairs within the vertical spacing between pairs of the containers 11. As a result, each of the lights extends in parallel along the length of a respective one of the containers 11. Positioning above the container allows each pair of lights 13 to cast illumination downwards along the entire top length of the wall structure 14 of the container. Such an arrangement may be better suited for biological materials that reside mostly on the top surface of the media.

The containers 11 in the embodiment illustrated by FIG. 4 are positioned in adjacent pairs of vertical stacks. The rack 12 in this embodiment includes vertical support members 17, but does not necessarily require the support rails 24, 26 to support the lights 13, unless needed for additional stability of the vertical support members. Extending inwards from the vertical support members are the cantilevered support members 19 (which are not shown in FIG. 4 for clarity) which may be connected at their ends to the ends of the cantilevered support members of the adjacent vertical stack of containers 11. Each pair of lights 13 is attached to the bottom of the retaining member 21 of the cantilevered support member above its respective one of the containers 11.

The relative arrangement of the containers 11 in FIG. 4 could also be accomplished by placing the front ends of two of the bioreactor assemblies illustrated in FIGS. 1 and 2 in an adjacent relationship. Such an arrangement would also combine the horizontally extending lights 13 of FIG. 4 with the vertically extending lights of FIGS. 1 and 2. Advantageously, the side-by-side relationship allows for overlap between the lighting of the adjacent vertical stacks of containers 11.

Another advantage of the side-by-side positioned vertical stacks of containers 11 shown in FIG. 4 is that density of the containers is improved while at the same time allowing the containers and lights 13 to be easily accessed for service. For instance, each pair of vertical stacks could be spaced so as to provide a service aisle 28 between them. In addition, the density of the stacks is still low enough that conventional building structures can provide support for the weight of the stacks. As is shown in FIG. 4, this allows the side-by-side stacks to be positioned on a mezzanine level 29 of the structure as well as the ground floor 30.

It should be noted that separate versions of the rack 12 are not described in additional details herein for the remaining embodiments because the aspects of the rack illustrated in FIGS. 1 and 2 can be extended to racks for supporting the containers 11 and lights 13 in the relative positions of the remaining embodiments. It should also be noted that although a preferred embodiment of the rack 12 is illustrated in FIGS. 1 and 2, various alternative configurations of the rack are possible with different materials, support member arrangements, etc., which will still support the containers 11 and lights 13 in their relative positions. In another example, the rack 12 may be constructed of interconnecting threaded rods with pipe collars to support the containers 11.

It should also be noted that the relative positions of the lights 13 and the containers 11, as well as the number of lights and containers, may be modified to suit a particular application. For instance, larger numbers of lights could be used to accelerate growth of the biological material, or larger numbers of containers stacked in a tighter arrangement may be used to grow larger amounts of biological material. Therefore, the combinations of lights and containers are not necessarily restricted to the above-listed configurations and would still fall within the scope of the present invention.

The wall structure 14 of each of the containers 11 is constructed of a light transmissive material which allows the passage of sufficient light to promote growth of the biological material stored in the reservoir 15 defined therein. For instance, the wall structure 14 may be constructed of a glass, such as a borosilicate or flint glass, or a plastic, such as a polycarbonate, polyvinylchloride, polystyrene, TEFLON, silicone, nylon or polyethylene. These materials may be either flexible or relatively rigid. Preferably, the light transmissive material not only allows the passage of some light, but is completely transparent to promote full passage of the light necessary to support growth. However, translucent materials may be used to screen out certain wavelengths or light intensities depending upon such factors as the needs of a biological material or the need to reduce the accumulation of heat in the reservoir 15.

The term "wall structure" herein refers to any member or collection of members that at least partially defines the reservoir 15. The wall structure 14 illustrated in the embodiment of FIGS. 1 and 2 has a cylindrical wall structure with a constant, circular cross-section along its length, which in this case is due to the use of a length of stock piping that is constructed of a transparent material. Preferably, the wall structure has a diameter that ranges from 2 to 12 inches and a length of 10 to 50 feet for growing biological materials of the duckweed family. Such dimensions typically allow 4 to 8 containers 11 to be stacked in a room with conventional ceiling heights. However, it should be recognized that any length or diameter of wall structure may be used as long as a proportionately large media surface can be provided for the growth of biological materials.

Other shapes could also be used for the wall structure 14 including shapes with, and without, a constant cross-section. For instance the wall structure may have a teardrop shape, or some arbitrary or irregular shape constructed to fit lighting needs or available space. Preferably, however, the shape is chosen to maximize the surface area of the portion of a cross-section of the reservoir 15 formed by the wall structure in a plane that is orthogonal to the pull of gravity (i.e., a horizontal plane). For instance, a wall structure 14 having a 6 inch diameter circular, cylindrical cross-section (the embodiment illustrated in FIG. 2) and 10 feet of length would have a maximum surface area (at the midpoint between its top and bottom) in the horizontal plane of 35 square feet.

Figure 5:
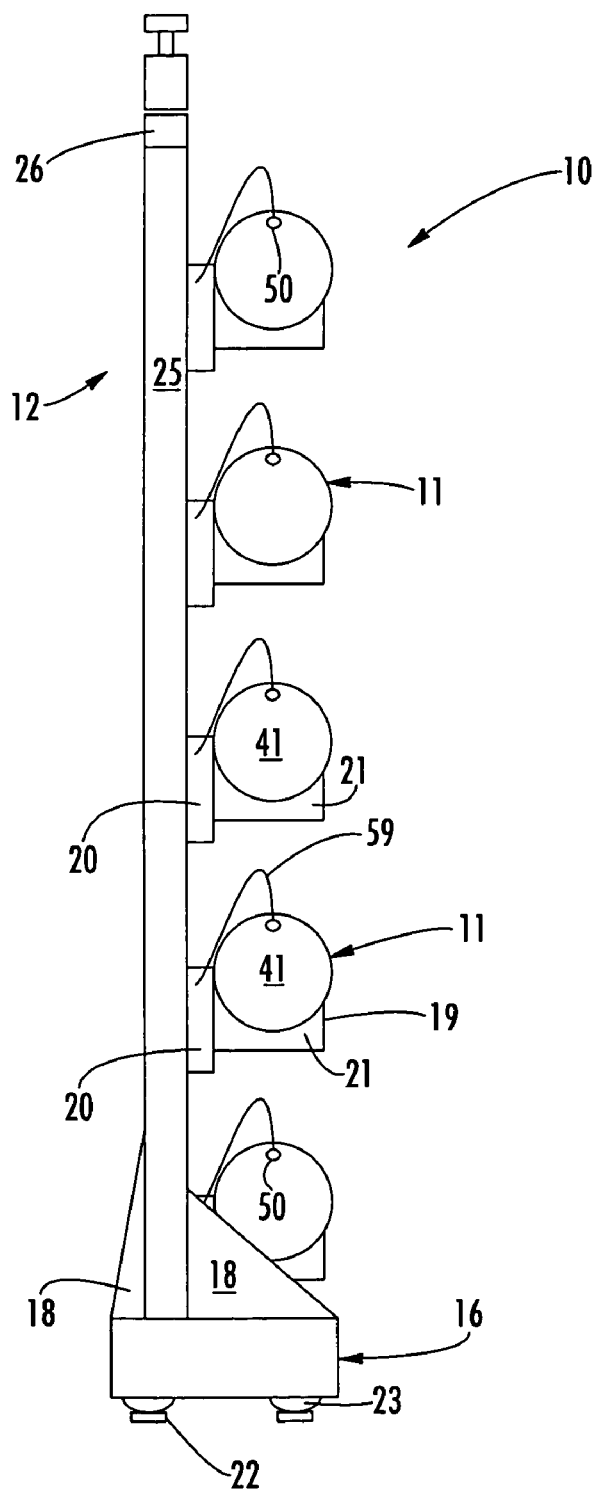
FIG. 5 is a side elevation view of a bioreactor assembly of another embodiment of the present invention using relatively large diameter containers.

An increase to a 10 inch diameter cross-section of a circular, cylindrical cross-section would result in an increase in media surface area to 42 square feet, as is shown by another embodiment illustrated in FIG. 5. However, the tradeoff due to the increase in height of the wall structure 14 is that fewer containers can be stacked within a limited vertical space.

Figure 6:
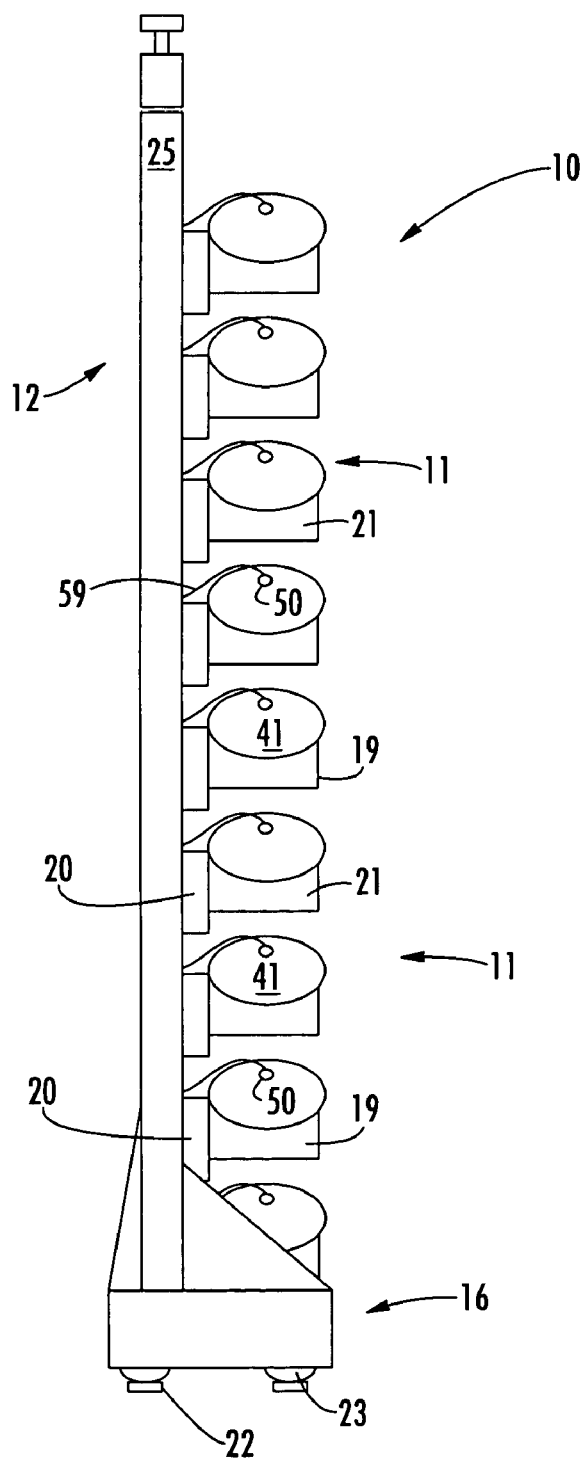
FIG. 6 is a side elevation view of a bioreactor assembly of another embodiment of the present invention using oval shaped containers.

In another embodiment, the cross-section of the wall structure 14 is an oval which has a major axis (i.e., its widest diameter) and a minor axis (i.e., its narrowest diameter), as is shown in FIG. 6. Advantageously, the major axis is oriented to be in the horizontal plane so as to maximize the top surface area of the media in the reservoir 15, while minimizing the height of the wall structure 14 so that more of the containers 11 may be stacked within a fixed vertical space. For instance, the illustrated oval cross-section having major axis of 11.1 inches oriented horizontally and a length of 10 feet the maximum media surface area is 83 square feet. In addition, the relatively short height still allows a large number of the containers 11 per vertical stack.

Figure 7:
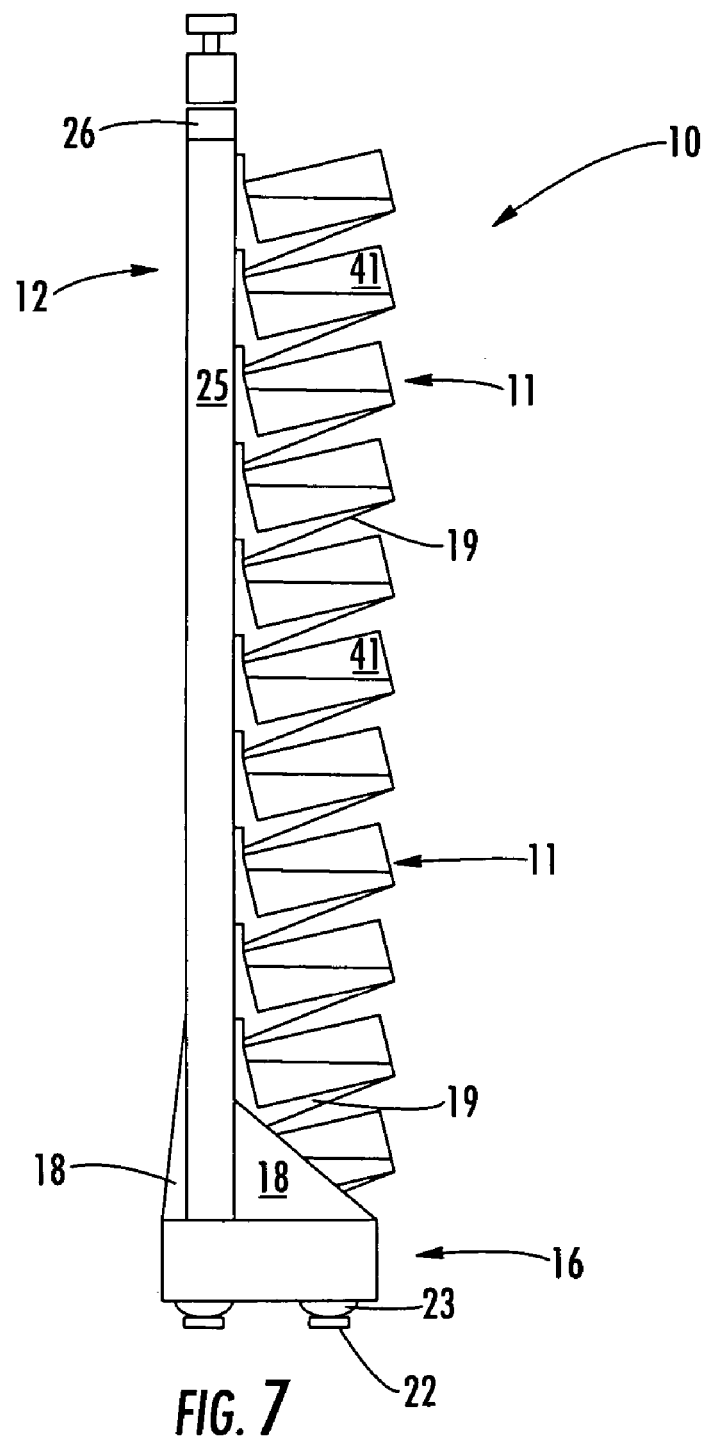
FIG. 7 is a side elevation view of a bioreactor assembly of another embodiment of the present invention using angled, rectangular shaped containers.

In yet another embodiment, the wall structure 14 has a rectangular cross-section with four corners, as is shown in FIG. 7. The horizontal cross-sectional area of the rectangular wall structure 14 is maximized by tilting the container so that two opposing corners are closer to, or in, the horizontal plane and the remaining pair of opposing corners are further away from the horizontal plane. For instance, a corner-to-corner distance of a 10 inch wide rectangular wall structure 10 feet in length results in a media surface area of about 98 square feet. Similar to the oval-shaped wall structure 14, a relatively large number of the rectangular containers 11 can still be employed in a limited vertical space. Alternatively, the rectangular wall structure 14 could be positioned so that its top and bottom are aligned with the horizontal plane.

Referring again to FIGS. 1 and 2, the wall structure 14 has a pair of ends wherein each of the ends is closed off by a clamp 40 and end cap 41 assembly. As is illustrated in more detail in FIG. 8, the end cap 41 is a circular plate of transparent material, preferably the same material as used in the wall structure 14, that is held against one otherwise open end of the wall structure 14. In addition, the end cap 41 may define one or more openings for access by various devices which will be described in more detail below. Alternatively, the end cap 41 could be constructed of translucent or opaque material if desired, especially if the wall structure 14 is relatively transparent.

Figure 9:
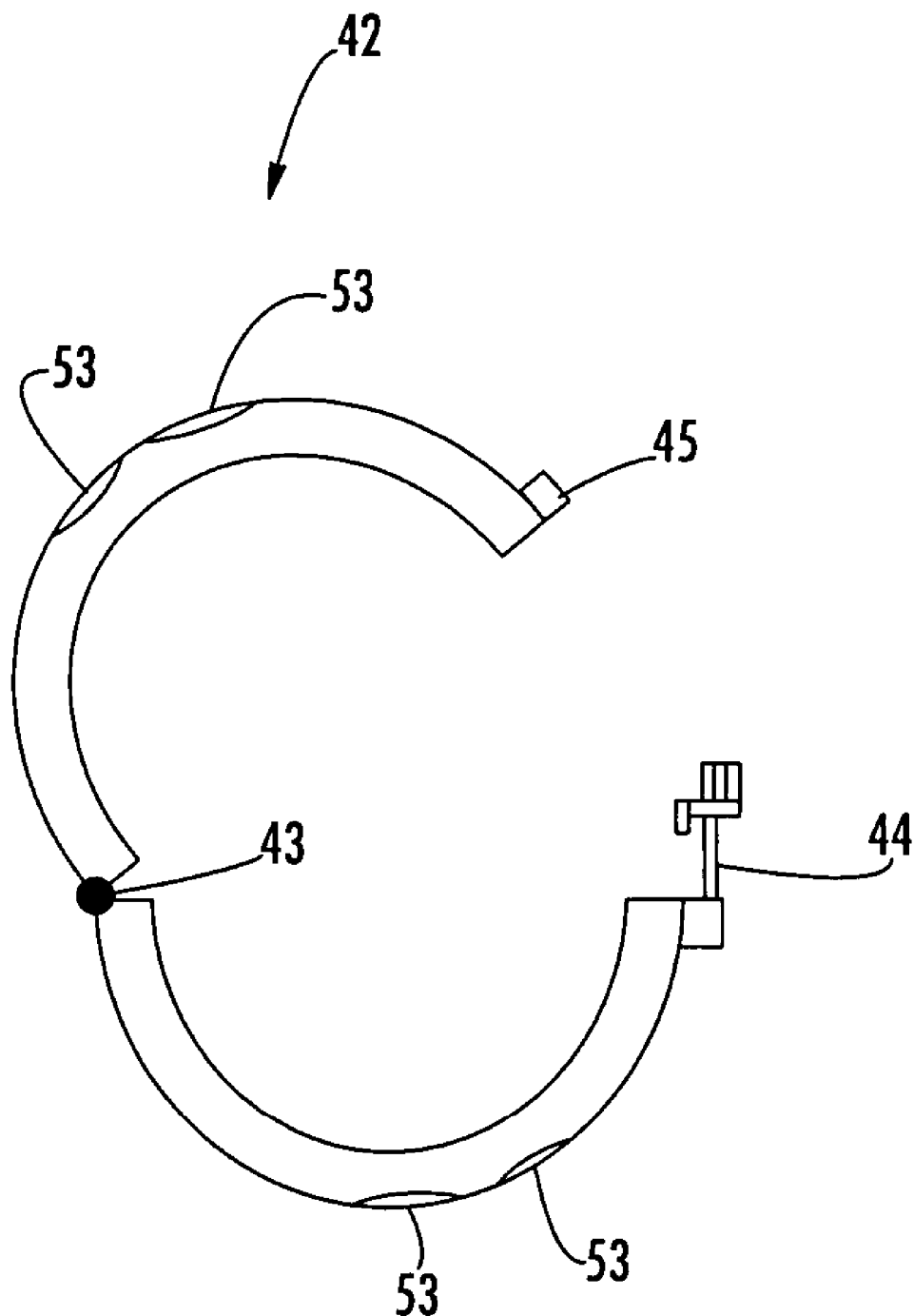
FIG. 9 is a plan view of an outer band portion of a clamp assembly of another embodiment of the present invention.

The clamp 40 includes an outer band portion 42 as shown in FIG. 9 which is split into two portions connected by a hinge 43. Opposite the hinge is a locking assembly that includes a screw 44 mounted on one of the portions and a threaded opening defined in a securing flange 45 on the other one of the portions. The outer band portion 42 with both portions connected has a circular shape with an inside diameter corresponding to the outside diameter of the circular cylindrical wall structure. In this manner, the outer band portion 42 can be opened to encircle the wall structure 14 and then secured by tightening the screw 44 in the securing flange 45, as shown in another embodiment of the present invention illustrated by FIG. 11. Of course, the size and shape of the outer band portion can differ so as to match the various sizes and shapes of the wall structures, such as those illustrated in FIGS. 5, 6 and 7.

Figure 8:
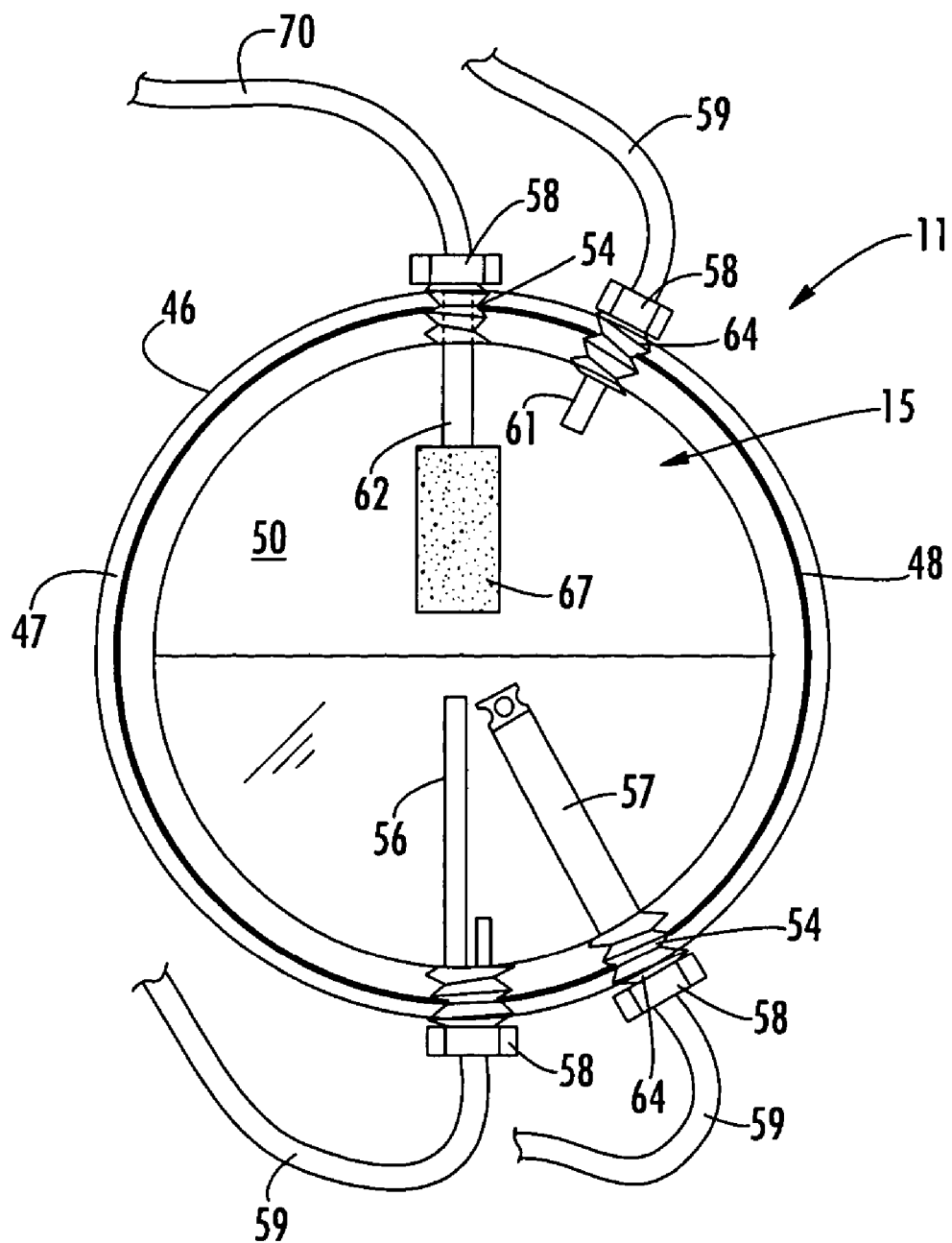
FIG. 8 is a side elevation view of an end of one of the containers shown in the bioreactor assembly of FIGS. 1 and 2.
Figure 10:
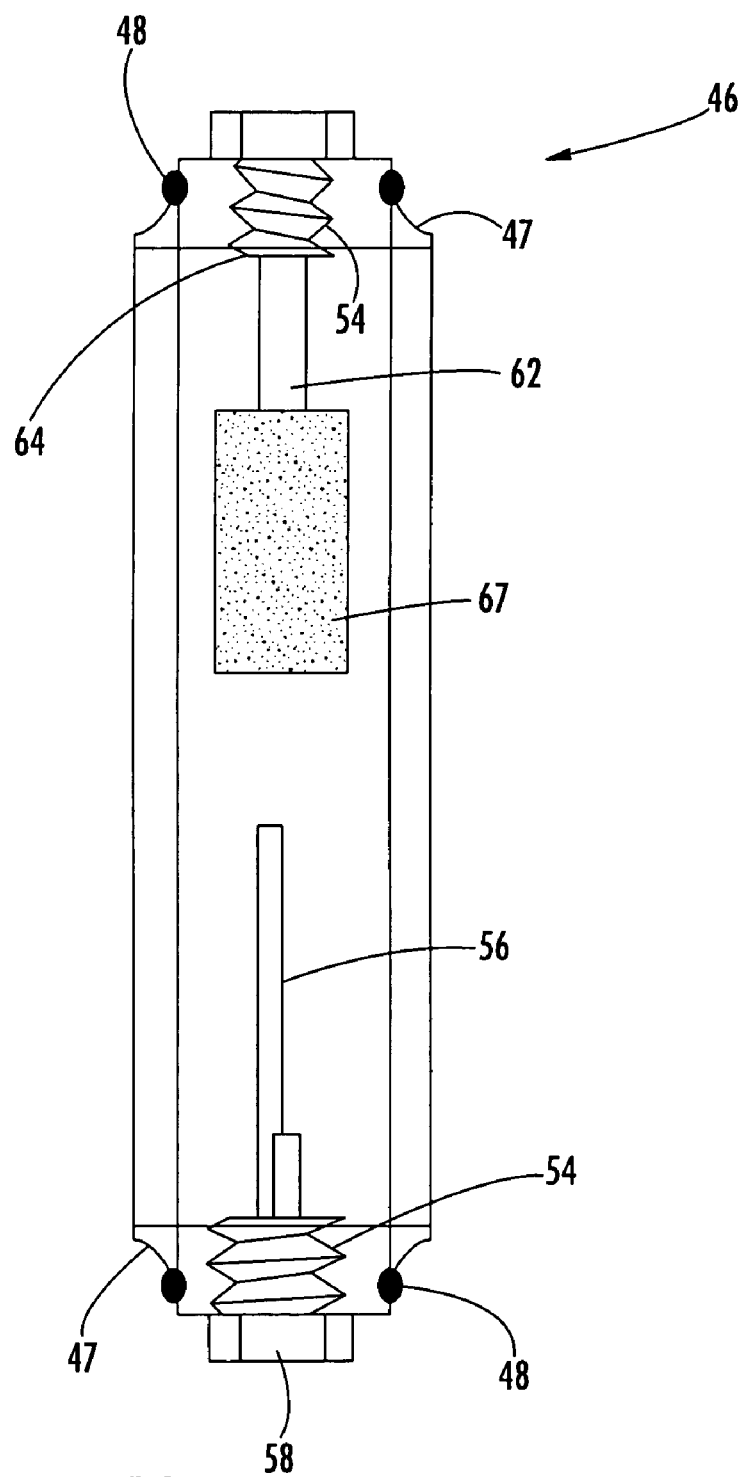
FIG. 10 is a plan view of an inner sealing portion for combination with the outer band portion shown in FIG. 9 to form the clamp assembly.

The clamp 40 also includes an inner sealing portion 46, as shown in FIG. 10. The inner sealing portion fitted for the circular, cylindrical wall structure 14 embodiment has the shape of circular, cylindrical ring sized to match the inner diameter of the wall structure, as is shown in FIG. 8. In particular, the sealing portion 46 includes a pair of chamfered edges 47 that are spaced across the body of the sealing portion. Each of the chamfered edges extends around the outer periphery of one of the sealing portion's ends and is sized and shaped to receive an end of the wall structure 14 or an edge of the end cap 41. The sealing portion may be constructed of a metal, such as stainless steel which is corrosion resistant, or an FDA approved composite material, such as acetyl copolymer, which is sufficiently stiff to compress the end cap 41 and wall structure 14 into sealing engagement.

Recessed within each of the chamfered edges 47 is preferably a seal 48, which in the illustrated embodiment is an O-ring having a circular cross-section. Such positioning of the seal 48 is advantageous because it is interposed and compressed between the end of the wall structure 14 or the edge of the end cap 41 when the outer band portion 42 is tightened thereon, as shown in the separate embodiment of FIG. 11. Preferably, the seal is constructed of an inert material, such as silicone, to maintain an aseptic environment in the reservoir 15 and prevent particulate contamination. However, other types of seals could be used that form a seal sufficient to maintain an aseptic environment in the reservoir 15. For instance, FDA approved elastomer materials such as the aforementioned silicone, polyethylene or rubber could be used for the seals.

Different seal configurations may be employed for different shapes and materials of the wall structure 14, end cap 41 or clamp 40. For instance, a gasket-type seal formed of a circular blank defining a hole therethrough could be employed between a wall structure having flat edge defining its end and an end cap that is a flat circular blank held onto the wall structure end using a latch and lever type clamp. In such a case the seal 48 may be constructed of a polymeric or metal material that need not be compressed as much to form a gas and liquid-tight seal due to the increased surface area over which it is applied.

Figure 11:
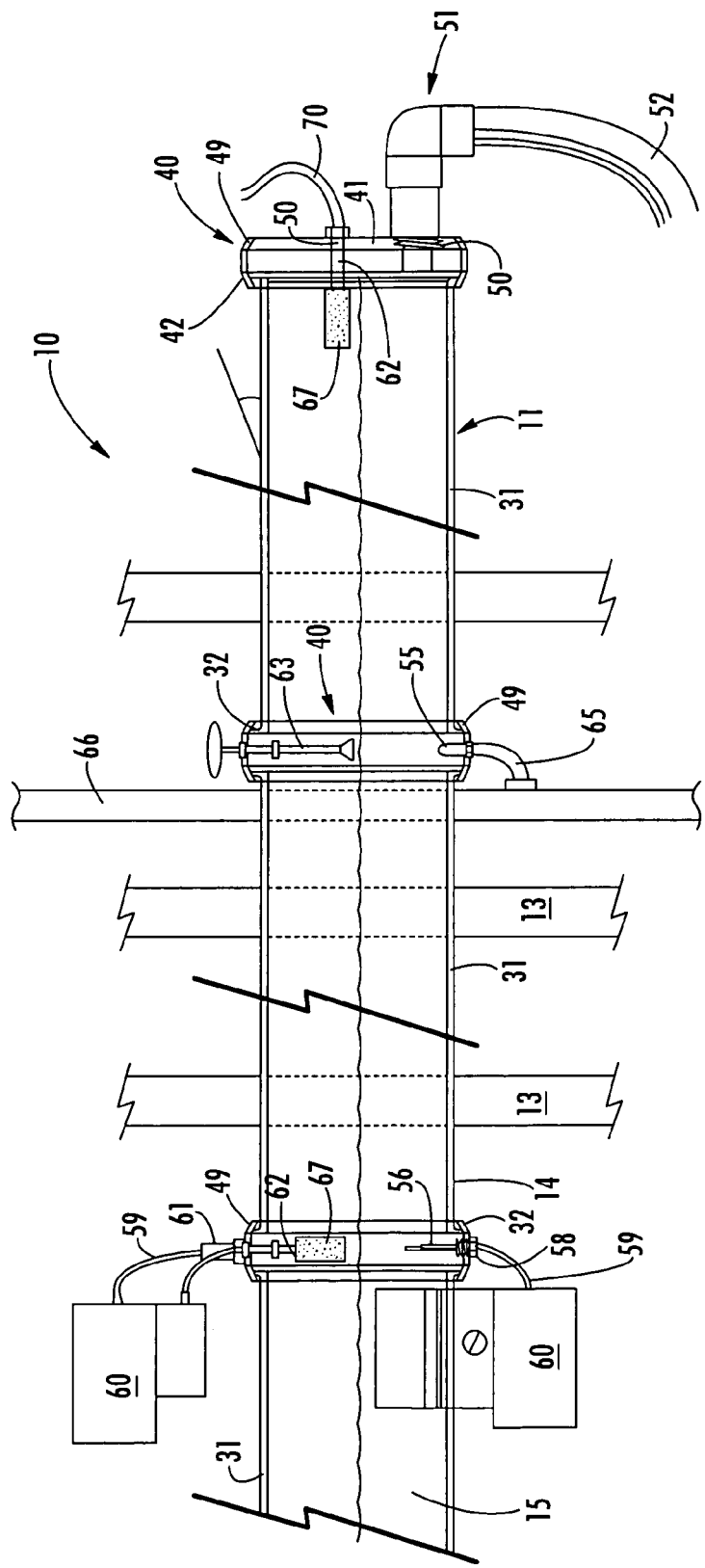
FIG. 11 is a side elevation view of a bioreactor assembly of another embodiment of the present invention where a wall structure of the container has multiple portions held together by clamps.
Figure 12:
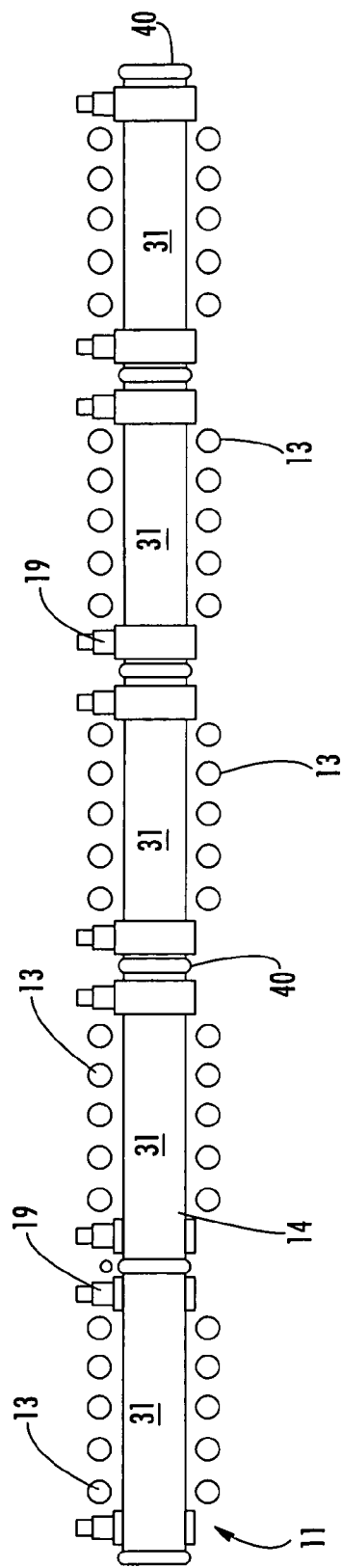
FIG. 12 is a plan view of the bioreactor assembly of FIG. 11.

In another embodiment of the present invention, the wall structure 14 of each of the containers 11 is split up into separate portions 31 joined together at adjacent ends by clamps 40, as shown in FIGS. 11 and 12. FIG. 12 illustrates the use of the separate portions 31 each supported by their own pair of respective cantilevered support members 19. In addition, the lights 13 extend vertically adjacent the front and back sides of the containers 11. Of course the multiple-portion container illustrated in FIG. 12 could be arranged in a large bank of other containers, as is illustrated by FIG. 3, or used in the various other embodiments illustrated and described herein in lieu of the containers having an integral wall structure without sub-portions. The multiple-portion wall structure 14, however, has the advantage of easy disassembly for compact transport and modifiability of the length of the containers 11.

As is shown in FIG. 11, one of the wall structure portions 31 has one end joined to an adjacent wall structure portion and is closed off by the end cap 41 at the other end. In particular, the end cap is held to the end of the wall structure portion by the clamp 40. Facilitating clamping attachment is a flared edge 32 that extend outwards in a radial direction at the ends of each of the wall structure portions 31. Preferably, the flared edge is rounded so as to fit snugly within the chamfered edges 47 of the clamp 40. In addition, the band portion 42 of each clamp 40 may have a pair of inwardly directed flanges 49 spaced apart on opposite ends of the band portion.

During assembly, the flared edge of the wall structure portion 31 is seated against the seal 48 and its respective chamfered edge of the sealing portion 46. Then, the inwardly directed flange at one end of the band portion 42 is extended over the outwardly directed flared edge 32 of the wall structure portion. As the band portion 42 is tightened, the inwardly directed flange 49 extends downwards onto the outer surface of the wall structure 14 at the base of the flared edge 32. This holds the flared edge by forming an inner diameter smaller than the diameter of the flared edge, thereby restraining the wall structure portion against axial movement.

In order to facilitate providing an aseptic environment while still allowing control of the environment within the reservoir 15, a plurality of threaded openings are defined through the inner band portion 42 and/or the end cap 41 to allow passage therethrough of various sampling, measurement and supply devices. Referring to FIG. 11, threaded openings 50 through the end cap allow the passage of main fill and drain nozzles 51. Each of these nozzles can receive or supply media and biological materials at a relatively high rate and therefore have relatively large diameters.

In addition, the nozzles 51 are attached to elbows and main fill and drain conduits 52 that extend downwards from the end cap 41. As is shown in FIGS. 1 and 2, the main fill and drain conduits 52 are preferably individualized to each of the containers 11 so that there is no cross-talk between the biological materials produced in one container with another container. Also, individualization isolates incidence of cross-contamination and allows the use of customized media for each of the containers. The nozzles 51 further provide the ability for clean-in-place (CIP) to pharmaceutical standards. Upstream, the fill conduits 52 may connect to a central header manifold from which the conduits branch, each having one or more valves to control flow.

As another option, the bioreactor assembly 10 may further include a disposable container liner that is configured to extend around the inside of each of the containers 11. For instance, such a liner could be inflatable to overly the portions of the container defining the reservoir 15 and translucent to allow light therethrough, or could be a translucent polymeric sleeve that slides into the wall structure 14. Advantageously, the container liner would promote cleaning procedures by being removable and disposable, allowing insertion of another container liner. Cleaning may also be facilitated through use of a special end cap 41 having particularly large openings defined therethrough for connection of large media extraction nozzles. Attachment of the end cap facilitates drawing of a vacuum in the reservoir 15 during media extraction.

Beyond primary supply and removal of the media, the media can be sampled and measured by other devices. For instance, openings 53 defined in the band portion 42 and threaded openings 54 defined in the sealing portion 46 of each clamp 40 can allow insertion and securing of a sampling nozzle 55, a multiple-level temperature probe 56 and a pH probe 57, as is shown in FIGS. 8, 10 and 11. As shown most clearly in FIG. 8 (wherein the band portion 42 of the clamp 40 is not shown for additional clarity), each of the probes can include a bolt head 58 attached at the end of a threaded portion 64 which allows the threaded portion to be advanced into the threaded opening 54 to secure it to the clamp 40. The sampling drain is attached similarly, as shown in FIG. 11. Although illustrated with the threads extending into the reservoir 15, the portion of the wall structure 14 most adjacent to the reservoir could define a relatively smooth cylindrical opening having a series of O-rings or other seals extending along its length to protect against leakage.

Extending from the threaded portion into the media is the probe (or nozzle) itself. For the probes, extending from the bolt head 58 are electrical leads 59 that connect to a conventional electronic measurement and control system 60. The sampling nozzle 55 has its own conduit 65 connected to a sampling and supply network 66. In this manner, the media can be measured for pH level, measured for temperature (at multiple levels in the media) or sampled for other measurements without opening of the containers 11 and the risk of contamination. Preferably, all of the threaded openings described herein are sealed against passage of contaminants, such as through use of polymeric tape, solder, a washer and seal combination, etc. As another alternative, once the threaded portion is secured within the threaded opening they could be welded, glued or otherwise permanently attached for a tight seal. Advantageously, for such permanent attachments threads may not even be required as long as the devices can be appropriately positioned during the welding or attachment process.

In addition to the supply, removal and measurement of media, air or other gasses in the reservoir 15 can be supplied, removed and measured using various other devices attached in a similar manner to the above-described devices. For example, additional threaded openings 50, 54 allow passage of an air temperature probe 61, a gas supply nozzle 62 and a gas exit nozzle 63. Each of these devices is secured in its respective threaded opening with its own bolt head 58 and threaded portion 64. The air temperature probe 61 allows the air temperature to be measured. Gas supply and exit nozzles 62, 63 allow control of the type, temperature, flow rate and other characteristics of the gasses in the reservoir 15. Preferably, the gas exit nozzle 63 is biased so as to allow flow in only a single direction, thereby preventing the infiltration of contaminants. At one end of the gas supply nozzle 62 is preferably a sparger 67 that diffuses the air supply so that it does not unduly disturb the media and biological matter within the reservoir 15. At the other end of the gas supply nozzle is a gas supply line 70.

It should be noted that other measurements within the reservoir 15 could also be made with a variation of other devices depending upon the information desired by the user. For instance, a gas composition probe could be used to sample the amount of $CO_2$ which would be used as feedback to modify the composition of gasses being added or removed by the nozzles 62, 63. The measurement, supply and removal devices discussed herein may also have different sizes, configurations and placements depending upon the desired frequency, accuracy, speed and other qualities of their performance.

In addition, the devices could also be extended through the container at other locations and portions of the containers 11 depending upon various needs of the user such as accessibility, tolerability of the container materials to openings, the risk of leakage and contamination, etc. For instance, the devices could extend through openings defined in the wall structure 14 or other components of the bioreactor assembly 10, in addition to the end cap 41 of the clamps 40. As another alternative a short section of the wall structure 14 (e.g., 4 to 6 inches in length) could define the openings for various devices. For instance, the nozzles 62, 63 could be supported and extend through the short section of wall structure and the short section of wall structure could be secured to the remaining wall structure with a victualic-type clamp. The short section could be removed and reattached for easy maintenance and cleaning.

The gas supply and removal nozzles 62, 63 could also be employed with a pump having sufficient power to reduce the gas pressure within the reservoir 15 prior to harvest of the biological materials in order to increase protein production by the biological materials. Alternatively, during a growth phase the gas pressure can be increased to promote growth of the biological materials in the reservoir. Notably, this is particularly effective for the media surface-borne plants which have large portions exposed to the gasses in the reservoir. Also, the air-tight construction of the reservoir of the present invention facilitates manipulation of the gas pressure therein.

It should be further recognized that although the illustrated clamp 40 is preferred for the illustrated wall structure 14 configurations, other types of clamps may also be employed herein to connect different portions of the bioreactor assembly 10. Alternative clamp configurations can address various factors, as desired, such as easy application and removal, firm attachment (which would benefit from the above-mentioned lever-type variation or a lever and ratchet design that allows progressive tightening), a complementary seal design that ensures an air and liquid-tight seal to ensure an aseptic environment within the reservoir 15, corrosion resistance, biocompatibility, use of acceptable materials under FDA regulations for pharmacological manufacturing processes and ability to support various measurement and sampling devices while maintaining the aseptic reservoir environment.

It should also be noted that although the above-described embodiments each has a continuous reservoir 15 extending in along a single major axis (i.e., a length extending in its longest dimension) and having a constant cross-section, the present invention should not be limited to such shapes. The wall structure 14, end cap 41 and other portions of the containers 11 defining the reservoir 15 can have several twists, turns, bifurcations and deviations as long as the media within the reservoir can be filled to a level defining a relative large media surface area for the support of surface-borne biological materials, such as duckweed plants.

Generally, this reservoir will have one or more major portions that each have a primary axis wherein the axes of all or most of the portions share a common plane. In this manner, the reservoir can be oriented (by orienting the container) until it is substantially horizontal (i.e., orthogonal to the pull of gravity) so that the flowable media forms the relatively large surface area. The term "substantially horizontal" is used herein because some angle in the major axis or axes may be desired to induce flow for processing purposes. For instance, the containers 11 illustrated in FIG. 1 have about a one inch drop per 50 feet in the direction of the main fill and drain nozzles 51 to facilitate fill and drain operations. A steeper drop could be used to further urge the media in the drop direction, but preferably the drop does not cause one end of the container to fill with media, or the media to fill to a height wherein the wall structure 14 prohibits full upwards growth of biological material on the media surface. Therefore, longer reservoir lengths 15 will typically require a less steep drop unless the reservoir is relatively tall compared to its length.

During initial use, the containers 11 are filled with the media using the main fill and drain nozzles 51 to supply relatively large volumes of the media. Biological materials can also be added using the main nozzles 51, or may be added when initially assembling the containers 11. Preferably, a surface-borne biological material is added such as plants from the duckweed family, or the aquatic plant species described above, that require light to proliferate via photosynthesis. As the reservoir 15 is filled it is monitored either visually, or automatically, to determine at which point the media reaches a level at which a maximized surface area is defined. In the case of the embodiment illustrated in FIGS. 1 and 2, this is at approximately the half-full point.

After the biological material and media are added, the power is supplied to the lights 13 (or the lights may have already been on) so as to cast light through the transparent wall structure 14 into the reservoir 15. Over time, the biological materials draw energy from the light and nutrients from the media and begin to proliferate. In the case of biological materials used for pharmacological purposes, the biological materials begin to secrete peptides and proteins into the surrounding media.

Also during this time, the various probes 56, 57, 61 are used to measure the properties (temperature, pH, $CO_2$ composition, etc.) of the gaseous and media environment in the reservoir. In turn, this data is collected and used to control the intensity of the lights 13, the temperature and convection properties of the ambient air around the containers 11, the temperature and amounts of gasses and media supplied to the reservoir 15 through the gas supply nozzle 62 and fill and drain conduits 52. In addition, the sampling nozzle 55 can be used to take small samples to determine the progress of the secretions. Such progress may also be used to determine the various aforementioned conditions within the reservoir 15.

At a certain point, such as when the media is exhausted or a complete harvesting of the biological materials is desired, the entire contents of the reservoir 15 can be flushed out of the main fill and drain nozzles 51 and conduits 52. After such flushing, cleaning compounds can be run through the system using the same nozzles and conduits. Alternatively, some type of steady state can be established wherein the expressed products of the biological materials can be continuous sampled, or partially drained, and the media and gasses refreshed, so that the growth and expression process is continues almost indefinitely.

The present invention has many advantages. Overall, the bioreactor assembly 10 allows the production of clinical and commercial scale quantities of biopharmaceuticals from genetically modified plants in a contained, aseptic environment. For example, the use of containers 11 defining reservoirs 15 for partial filling with media provides a relatively large surface for the large-scale production of surface-borne biological materials, such as duckweed plants. In addition, use of the clamps 40 having seals to interconnect the various portions of the container wall structure 14 and sealed openings 50, 54 for insertion of various measurement and supply devices ensures a clean and aseptic environment to promote the growth of the biological materials for medical uses. The clamping system also allows for easy assembly and disassembly of the containers 11 for maintenance and modification. The measurement and supply devices ensure that the environment within the reservoir 15 is tightly controlled to maximize growth and expression of the biological materials therein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An assembly for holding a media and supporting growth of a biological material requiring light for proliferation, said assembly comprising:
    at least one light source; and
    at least one container positioned adjacent the light source, said container having a light transmissive wall structure defining an elongate, aseptic reservoir, said elongate reservoir having a major axis with a substantially horizontal orientation wherein said reservoir is capable of being partially filled with media so as to create a media surface on which the biological material is supported, wherein said at least one container further includes at least one clamp and wherein the container wall is divided into at least two portions, wherein each of said portions has an open end and wherein the ends of the portions are adjacent and held together with a clamp.

2. An assembly according to claim 1, wherein the wall structure has a constant cross-section along said major axis.

3. An assembly according to claim 2, wherein the cross-section is a circular cross-section.

4. An assembly according to claim 2, wherein the wall structure is between 10 and 50 feet in length.

5. An assembly according to claim 4, wherein the wall structure has a diameter from between 2 to 12 inches.

6. An assembly according to claim 2, further comprising end caps secured to open ends of the wall structure.

7. An assembly according to claim 1, additionally including a rack, with a plurality of said containers supported by said rack and arranged in a vertical stack with spacing therebetween.

8. An assembly according to claim 7, wherein the light source includes a plurality of electrically powered lights positioned on opposite sides of the vertical stack.

9. An assembly according to claim 1, wherein the wall structure has a constant oval-shaped cross-section along said major axis and wherein the oval shaped cross-section has a major axis extending in the substantially horizontal plane.

10. An assembly according to claim 1, wherein the wall structure has a constant cross-section along said major axis and wherein the cross-section has a rectangular shape with two opposite corners of the rectangular shape structure positioned closer to the substantially horizontal plane than the remaining two opposite corners.

11. An assembly according to claim 1, wherein the clamp defines an opening sized and shaped to receive the adjacent ends of the wall structure portions.

12. An assembly according to claim 11, wherein the clamp includes a central band extending around the clamp opening and having a pair of inwardly directed flanges spaced apart on opposite ends of the clamp, said flanges configured to grip the ends of the wall structure portions.

13. An assembly according to claim 12, wherein the ends of the wall structure portions flare outwards to engage the inwardly directed flanges.

14. An assembly according to claim 13, wherein the clamp further includes a seal extending along the flanges between the flared ends of the walls structure portions and the inwardly directed flanges of the clamp.

15. An assembly according to claim 14, wherein the clamp is constructed of an FDA approved composite material.

16. An assembly according to claim 14, wherein the seal is an FDA approved elastomeric material.

17. An assembly according to claim 1, further comprising at least one of a gas supply nozzle, a gas exit nozzle, an air temperature probe, a pH probe, a sampling drain, a gas composition probe and a media temperature probe extending into the reservoir through an opening defined by the container.

18. An assembly for holding a media and supporting growth of a biological material requiring light for proliferation, said assembly comprising:
    a support rack;
    a plurality of elongate laterally extending containers carried by said support rack and arranged in a stack spaced apart vertically from one another, each container having a light transmissive wall structure defining an elongate, aseptic reservoir, said elongate reservoir having a major axis with a substantially horizontal orientation wherein the reservoir is capable of being partially filed with media so as to create a media surface on which the biological material is supported; and
    at least one light source carried by said support rack and mounted adjacent to said containers for illuminating the containers, wherein said at least one light source comprises a plurality of elongate fluorescent tubes mounted to said rack and wherein the tubes extend vertically and are laterally spaced from one another.

19. An assembly according to claim 18, wherein said support rack includes a plurality of upright support members, and upper and lower laterally extending support rails interconnecting said upright support members, and wherein said containers are mounted to said upright support members.

20. An assembly according to claim 18, wherein each of said containers comprises an elongate transparent tube of substantially uniform cross-section, and end caps closing opposite ends of said tube to define said elongate reservoir.

21. An assembly according to claim 20, wherein each of said containers includes at least two elongate transparent tube sections mounted end-to-end, and a clamp interconnecting the adjoining end portions of the tube sections.

22. An assembly according to claim 18, wherein the tubes extend substantially horizontally and generally parallel to the containers.

23. A method of growing in a liquid media a biological material requiring light for proliferation, said method comprising:
   providing at least one light transmissive container defining a reservoir having a major axis with a substantially horizontal orientation;
   filling the reservoir with the liquid media until a partial fill level is reached so as to define a top surface of the media extending along a length of the reservoir;
   adding the biological material to the reservoir and supporting the biological material on the top surface of the media;
   exposing the container to a light source so as to promote growth of the biological material via photosynthesis;
   heating and circulating the media; and wherein providing the light transmissive container includes clamping portions of the light transmissive container together using one or more clamps.

24. A method of claim 23, further comprising sealing the reservoir against contamination after filling the reservoir with liquid media and adding the biological material.

25. A method of claim 23, further comprising accessing the reservoir through an opening defined in the container.

26. A method of claim 25, wherein accessing the reservoir includes inserting a gas supply nozzle through the clamp opening and supplying gas to the reservoir.

27. A method of claim 25, wherein accessing the reservoir includes inserting a temperature probe through the clamp opening and measuring a temperature within the reservoir.

28. A method of claim 25, wherein accessing the reservoir includes inserting a pH probe through the clamp opening and measuring a pH of the media within the reservoir.

29. A method of claim 25, wherein accessing the reservoir includes draining a sample through the clamp opening.

30. A method of claim 23, wherein filling the reservoir includes supplying the media through an opening defined in an end of the container.

31. A method of claim 23, further comprising draining the liquid media from the reservoir after filling the reservoir.

32. A method of claim 23, further comprising automatically measuring and controlling one of a temperature, a media pH, the media fill level, gas pressure and gas concentration.

33. A method of claim 23, further comprising supplying conditioned air around the container to control a temperate within the reservoir.

34. A method of claim 23, further comprising mounting a plurality of the containers in a stack spaced apart vertically from one another.

* * * * *

UNITED STATES PATENT AND TRADEMARK OFFICE
CERTIFICATE OF CORRECTION

| | |
|---|---|
| PATENT NO. | : 7,176,024 B2 |
| APPLICATION NO. | : 10/845914 |
| DATED | : February 13, 2007 |
| INVENTOR(S) | : Branson et al. |

It is certified that error appears in the above-identified patent and that said Letters Patent is hereby corrected as shown below:

<u>Column 15,</u>
<u>Line 31</u>: "photosynthesis;" should read --photosynthesis; and--

Signed and Sealed this

Nineteenth Day of June, 2007

JON W. DUDAS
*Director of the United States Patent and Trademark Office*